United States Patent
Tan et al.

(10) Patent No.: US 7,106,763 B2
(45) Date of Patent: Sep. 12, 2006

(54) WAVELENGTH CONTROL FOR CAVITY RINGDOWN SPECTROMETER

(75) Inventors: Sze Tan, Sunyvale, CA (US); Bernard Fidric, Cupertino, CA (US); Barbara Paldus, Portola Valley, CA (US); Eric Crosson, Sunnyvale, CA (US)

(73) Assignee: Picarro, Inc., Sunnyvale, CA (US)

( * ) Notice: Subject to any disclaimer, the term of this patent is extended or adjusted under 35 U.S.C. 154(b) by 358 days.

(21) Appl. No.: 10/803,827

(22) Filed: Mar. 18, 2004

(65) Prior Publication Data

US 2005/0206903 A1 Sep. 22, 2005

(51) Int. Cl.
*H01S 3/10* (2006.01)
(52) U.S. Cl. ............................................. 372/9; 372/33
(58) Field of Classification Search ..................... 372/9
See application file for complete search history.

(56) References Cited

U.S. PATENT DOCUMENTS 6,048,105 A * 4/2000 Ohtomo et al. ............... 385/88
2002/0126724 A1* 9/2002 Tsunekane et al. ........... 372/69

* cited by examiner

*Primary Examiner*—Minsun Oh Harvey
*Assistant Examiner*—Dung Nguyen
(74) *Attorney, Agent, or Firm*—Lumen Intellectual Property Services, Inc (57) ABSTRACT

A cavity ring-down spectrometer includes:
  a) multiple detectors for monitoring the intensity of the radiation emitted from the cavity and the wavelength of the radiation injected into the cavity;
  b) controllers which turn off the radiation into the cavity and precisely adjust the temperature of, and current to, the laser gain medium; and
  c) means for adjusting the beam path length of the optical cavit to bring the cavity into resonance with the injected radiation. Additionally, disclosed is a method for using the spectrometer to detect a target analyte.

14 Claims, 5 Drawing Sheets

WAVELENGTH CONTROL FOR CAVITY RINGDOWN SPECTROMETER

FIELD OF THE INVENTION

This invention relates to absorption spectroscopy and, in particular, to cavity ring-down spectroscopy (CRDS). In particular, this invention relates to an apparatus and method for controlling the input of laser light into the resonant optical cavity of a CRDS instrument.

BACKGROUND OF THE INVENTION

Cavity Ring-Down Spectroscopy (CRDS) is an increasingly widely used technique for detecting and monitoring analytes, especially when the target analyte is present in very low concentration. Techniques are available which enable the use of CRDS with gaseous, liquid or solid samples. Various aspects of CRDS are described in numerous U.S. Patents such as U.S. Pat. Nos. 5,815,277, 5,903,358, 5,912,740, 6,084,682, 6,094,267, 6,233,052, 6,377,350, 6,452,680, 6,466,322 and 6,532,071. Cavity Ringdown Spectroscopy by K. W Busch and M. A Busch, ACS Symposium Series No 720, 1999 ISBN 0-8412-3600-3, gives a comprehensive, generally up to date overview of many aspects of CRDS technology.

In essence, CRDS involves measuring the decay time of a photon filled, high finesse resonant optical cavity (the ring-down cavity). The cavity is formed by from two to usually three or four ultra-high reflectivity dielectric mirrors, which comprise the optical resonator. Monochromatic light from a laser is injected into the cavity which encloses the analyte sample. The decay time is determined by:

i) the round trip path length of the optical beam within the cavity;
ii) losses inherent in the cavity itself (primarily diffraction losses and losses through the mirrors); and
iii) most importantly, losses due to the frequency dependent losses due to absorption by the target analyte.

Since losses i) and ii) are independent of the analyte, the analyte spectrum is determined by the frequency dependent decay time of the resonant cavity with the target analyte present.

A major advantage of CRDS relative to conventional absorption spectroscopy is that it does not depend on a power-ratio measurement but rather provides an absolute measurement (i.e, decay time).

As above-indicated, cavity ring-down spectroscopy involves measuring the absorption of radiation by a sample via the effects of this absorption on the decay rate (the "ring-down time constant") of an optical cavity. The absorption is measured as a function of the wavelength of light resonating in the cavity to obtain the desired spectrum and/or concentration of a target analyte.

The optical cavity is initially filled with radiation from a laser, and ring-downs are initiated by interrupting this incoming radiation. It is important for the purposes of high-resolution spectroscopy that the wavelength of the laser be precisely known at the time each ring-down occurs. In the present invention the cavity length is adjusted so that (a mode of) the cavity is in resonance with the laser radiation at the time of ring-down. Due to the resonance condition, the intra-cavity intensity builds up rapidly while the laser is on. The accuracy to which the ring-down time constant can be measured improves with increasing intra-cavity optical intensity, so it is desirable to make this quantity (the "cavity filling") as large as possible.

Several factors limit how much cavity filling can be achieved in practice. Due to the very high finesse (or very narrow line width) of the cavity, small fluctuations in the laser wavelength (or the cavity length) can cause the incident light to go into and out of resonance with the cavity. When this happens, the intra-cavity intensity may decrease or fluctuate irregularly while the laser remains turned on. In addition, filling uniformity also affects the repetition rate and hence measurement speed. It is therefore doubly important for the laser to have minimal frequency jitter. For a semiconductor laser, the wavelength is a very sensitive function of both the pump current to, and the temperature of, the laser, making the control of these quantities very important. In particular, achieving good cavity filling at each of a collection of wavelengths (as required for a spectral scan) requires a very low-noise current source and the ability to control the laser pump current over a moderately wide bandwidth (of the order of the inverse cavity lifetime) to maintain the laser output at the desired wavelength set point while the cavity fills up.

Figure 1:
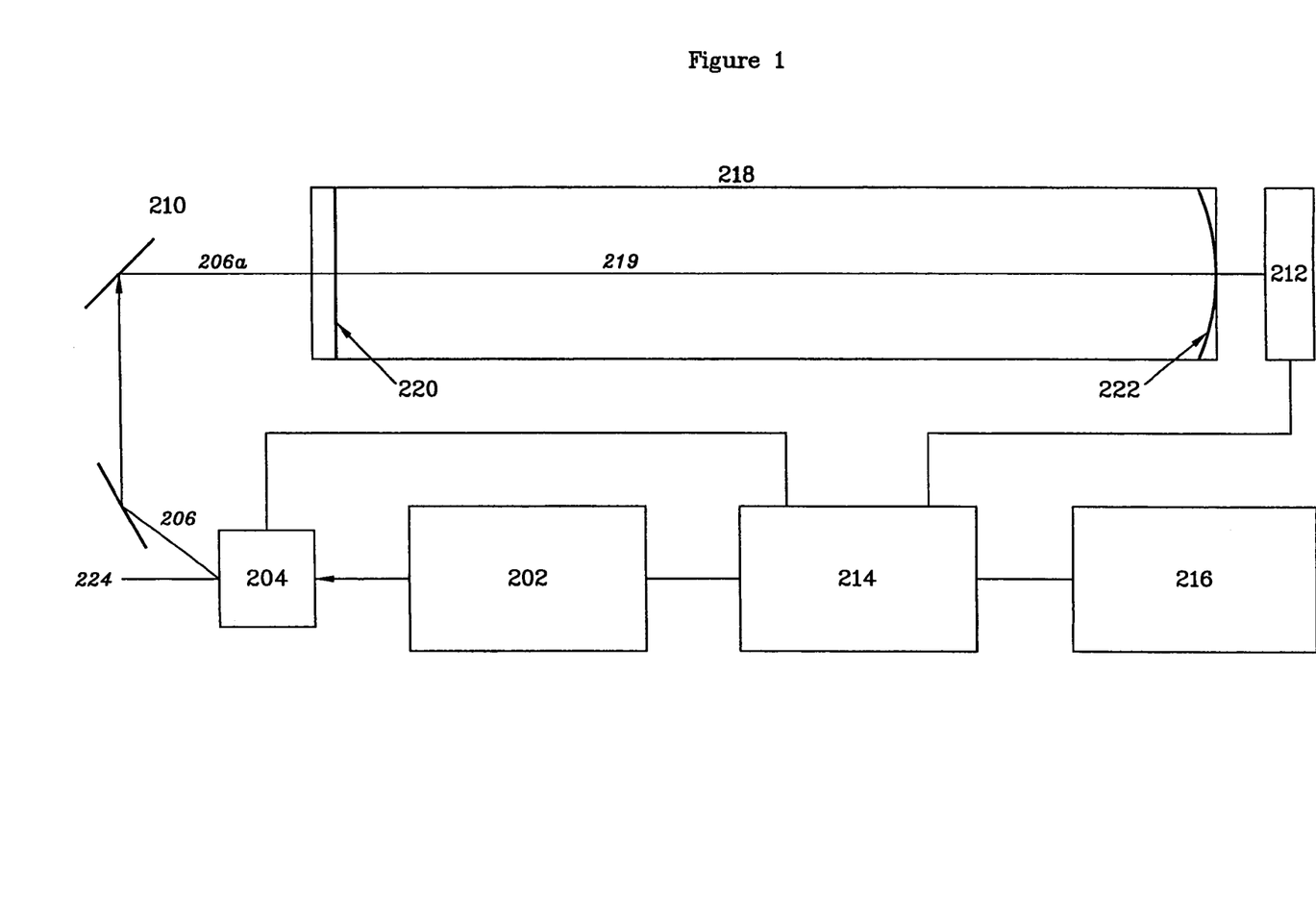
FIG. 1 shows a prior art system for controlling a laser light source.

A conventional two-mirror, continuous wave (CW) CRDS instrument (200) is shown in FIG. 1.

As shown in FIG. 1, light is generated from a narrow band, tunable, continuous wave diode laser 202. Laser 202 is temperature tuned by a temperature controller (not shown) to emit its radiation at a wavelength approximately equal to a desired spectral line of the analyte. An acousto-optic modulator (AOM) 204 is positioned in front of the radiation emitted from laser 202. AOM 204 provides a means for providing light 206 from laser 202 along the optical axis 219 of resonant cavity 218. Light 206 exits AOM 204 and is directed by mirrors 208 and 210 to cavity mirror 220 as light 206a which travels along optical axis 219 and exponentially decays between cavity mirrors 220 and 222 when light 206 is extinguished or deflected from the cavity axis. The measure of this decay is indicative of the presence or lack thereof of a trace species. Detector 212 is coupled between the output of optical cavity 218 and controller 214. Controller 214 is coupled to laser 202, processor 216, and AOM 204. Processor 216 processes signals from optical detector 212 in order to determine the level of trace species in optical resonator 218.

In AOM 204, a pressure transducer (not shown) creates a sound wave that modulates the index of refraction in an active nonlinear crystal (not shown), through a photoelastic effect. The sound wave produces a Bragg diffraction grating that disperses incoming light into multiple orders, predominantly zero order and first order. Different orders have different light beam energy and follow different beam directions. In CW-CRDS, typically, a first order light beam 206 is aligned along with optical axis 219 of cavity 218 incident on the cavity in-coupling mirror 220, and a zero order beam 224 is idled with a different optical path (higher order beams are very weak and thus not addressed). Thus, AOM 204 controls the direction of beams 206 and 224.

When AOM 204 is on, most light power (typically, up to 80%, depending on size of the beam, crystals used in AOM 204, alignment, etc.) goes to the first order along optical axis 219 as light 206. The remaining beam power goes to the zero order (light 224), or higher orders. The first order beam 206 is used for the input coupling light source; the zero order beam 224 can be used for diagnostic components. Once sufficient light energy is built up within the cavity, AOM 204 is turned off. This results in all the beam power going to the zero order as light 224, and no light 206 is coupled into resonant cavity 218. The light energy inside the cavity then follows an exponential decay (i.e., "rings down").

In order to "turn off" the laser light to optical cavity 218, and thus allow for energy within optical cavity 218 to ring down, AOM 204, under the control of controller 214, redirects (deflects) light from laser 204 along path 224 and thus away from optical path 206 into optical resonator 218.

Some art workers have endeavored to provide an alternative to using an AOM to turn off the transmission of photons into the optical cavity. For example, the system described in WIPO applications 03/098173 (US 2003/0210398) is reported to function as follows:

i) a controller deactivates (shuts off) the laser light source when the light emitted from the cavity reaches a predetermined threshold. The laser is turned off by shunting the laser current away from the laser;

ii) the laser remains shut off for a fixed period significantly exceeding the ring-down time and the cavity rings-down during the initial portion of the fixed shut-off period and the concentration of the target analyte is thereby measured;

iii) the light source is turned back on at the end of this first shut-off period to thereby initiate a second fixed period during which the restarted laser "stabilizes". By setting the laser temperature to an appropriate value, by the end of this period the laser emission frequency should be stabilized at a value which is approximately correct for a given target analyte. The current to the laser is then modulated to more finely vary the laser emission frequency until it coincides with a cavity resonance mode at some point during the modulation resulting in energy build-up within the fixed length cavity. While this system may sometimes have advantages over a system using an AOM to turn off the light into the optical cavity, it is not capable of achieving the degree of precision achievable with an optimized CRDS instrument in accordance with the present invention.

Since the laser emission wavelength depends both on temperature and pump current, adjusting the laser temperature to a preset value so as to provide a nominal (in reality only approximately correct) wavelength, and subsequently modulating the current, can cause the actual laser wavelength to differ significantly from the desired value. It is not possible to do high-resolution spectroscopy with such a configuration. Equally significant, in this method no mechanism to compensate for the effects of laser aging. It is well known in the laser art that over time the temperature and current required to achieve a particular emission wavelength will change. The above design does not provide a feedback mechanism to detect or compensate for the effects of aging so that over time the instrument will tend to drift away from the analyte absorption feature which it is trying to detect.

SUMMARY OF THE INVENTION

In the system of the present invention, both the temperature of and current to the laser are continuously monitored and adjusted to bring the laser emission to the desired wavelength to within a frequency accuracy of approximately 10 MHz (0.0003 cm$^{-1}$). An additional wavelength monitor unit is required for this purpose, and this is used in conjunction with a hardware control loop, which adjusts the laser current. With the help of this control loop, the time to stabilize the laser wavelength is only a few hundred microseconds, as compared to the at least 100 ms required by the above-described prior art systems.

An object of the present invention is to provide an improved control system for CW Cavity Ring-Down Spectrometers. In particular, the present invention is directed to an apparatus and method for precisely controlling the wave length of the light used to illuminate the resonant cavity of a CRDS instrument.

A Cavity ring-down spectrometer includes the following components:

i) the resonant optical cavity which comprises at least two, and preferably three or four, high reflectivity mirrors;

ii) an electrically pumped, semiconductor laser which may, for example, be an external-cavity diode laser (ECDL) or preferably a distributed feedback (DFB) diode laser. The laser provides the light (radiation) which is emitted into the resonant cavity. The wavelength of the radiation produced by the gain medium is dependent on both the temperature of the gain medium and the current pumped into it. For purposes of spectroscopy it is necessary to provide means to tune, i.e., alter the wavelength of the light emitted by the gain medium into the optical cavity to be close to a wavelength absorbed by a target analyte species or to scan over a specific absorption feature. Alternatively, a DBR (Distributed Bragg Reflector) laser can be utilized. Alternatively, an array of DFB or DBR lasers on a single chip, with the lasers of the array having contiguous tuning ranges, can be utilized to provide a broadly tunable system. In such a case the system which controls the laser emission wavelength as hereinafter described, will first select from the array a particular DFB of a desired emission wavelength.

iii) means for turning off (deactivating) the optical signal into the resonant cavity when the laser is at the desired wavelength and the cavity contains photons in a quantity above a threshold level. The threshold is basically determined by the inherent signal to noise ratio of the particular instrument, i.e., the higher the ratio the lower the threshold, i.e., the number of photons in the cavity, required to obtain good spectroscopic results. "Turning off" the light into the cavity permits it to "ring-down". After the cavity has "rung-down" light from the laser is again directed into the optical cavity to fill it up to the threshold level, the optical signal is again turned off and the ring-down process repeated. The distinctive spectrum for any given analyte results from performing the ring-down process over a more or less broad range of wavelengths.

As already indicated, there are a number of conventionally used methods for deactivating the optical signal into the resonant optical cavity in order to permit the cavity to ring-down:

i) change the beam path so that it no longer is aimed at the cavity input mirror;

ii) periodically turn off the current to the laser;

iii) periodically shunting the current to an alternative medium preferably one having electrical properties (e.g., resistance, capacitance and/or inductance) similar to the gain medium;

iv) frequency shift the laser emission out of the resonance range of the cavity by varying the laser input current.

Normally, in methods i) and iv) the laser remains on at all times. The first method conventionally utilizes an acousto-optic modulator (AOM), as previously described. One approach which utilizes the second method is described in previously mentioned published U.S. Application 2003/0210398. In methods ii) and iii) the current flow to the gain medium is turned off (terminated) thereby temporarily deactivating the optical signal.

The present invention is directed to a CRDS instrument and method which sequentially activates (turns on) and shuts off (deactivates) the light into the resonant optical cavity using any one of methods ii) through iv), above. However, the method and apparatus of the present invention differs significantly and advantageously from any of the prior art methods and apparatus, including that described in the afore-mentioned published application.

The method of the present invention includes the following steps:

i) directing a continuous wave optical signal, preferably from a semi-conductor diode laser, into a resonant optical cavity comprising at least two high reflectivity mirrors;

ii) using a first detector to monitor the radiation emitted from the optical cavity through one of these mirrors and determine when the intensity of the emitted radiation is equal to a pre-determined threshold value. Suitable detectors include, for example, photodiodes, avalanche photodiodes and photo-multiplier tubes. The power of the radiation impinging on the detector is equal to the power of the radiation circulating in the resonant cavity multiplied by the power transmission coefficient of the output mirror. The threshold must be sufficient to provide an adequate signal to noise ratio and thereby provide an accurate determination of the ring-down decay constant (normally referred to as $\tau$).

iii) using a first controller to deactivate the laser by turning off or shunting the current, thereby interrupting the current flow to the gain medium to thereby permit the cavity to ring-down.

iv) reactivate the laser by again passing current into the gain medium and thereby cause it to again direct an optical signal into the optical cavity. Note that in this arrangement the laser is alternately on and off, but when on is always positioned to direct its optical beam into the cavity and the emission wavelength is being continuously monitored by a second controller to provide active feedback which enables precise control of the laser emission wavelength.

As an alternative to steps iii) and iv) the optical signal can be deactivated by frequency shifting the laser emission frequency out of the resonance range of the optical cavity or by use of a beam redirecting AOM as previously described. Reactivation is achieved by returning the input current to a value which brings the laser output back into the resonance range of the cavity. In this alternative embodiment the laser is always "on".

When a DFB or other semiconductor laser is maintained at constant temperature and the pump current is raised from zero to a constant value, the wavelength of the laser changes rapidly (over up to a few tenths of a nm) before approaching its steady-state value on a timescale of a about a few milliseconds, which limits data acquisition rates. We have found that by using a feedback circuit to vary the laser current, while simultaneously monitoring the laser wavelength, it becomes possible to significantly reduce the time required to obtain a desired wavelength having the stability needed for efficient cavity filling. This significantly reduced the response time of the CRDS instrument. Suitable laser wavelength monitoring can be effected by the use of an etalon in either transmission or reflection, a linear transmission filter or a combination of the foregoing.

In consideration of the above, a cavity ring-down spectrometer in accordance with the present invention performs the following steps.

In a preferred procedure, two look-up tables are constructed, one to record the approximate (coarse value) gain medium temperature and a second to record the current required for the laser to produce a particular desired emission wavelength in the steady state. When using a laser array, such a "look-up table" is made for each laser in the array. In contrast to the prior art, in our design, because the laser emission wavelength is substantially continuously monitored, the look-up table can be continuously updated during the laser's service life to ensure that the instrument emits at the desired wavelength notwithstanding any changes in the laser itself as a result of aging effects.

At the beginning of each ring-down cycle, the laser is turned on (methods ii) and iii), its emission frequency returned to a value within the resonance range of the cavity i.e., method iv), or the beam path realigned to the cavity (method i) with the temperature and current being set to the tabulated coarse values to approximately achieve a desired wavelength. At this time an error signal processor which forms part of the second controller is in the reset state, and produces zero output. The output control (which determines input current to the laser diode) for the pump current source is adjusted to the pre-tabulated coarse value. The error signal processor then commences to function in its normal operating state. The input to the processor is the wavelength error signal, which is obtained by noting the difference between the desired wavelength and the laser output as measured by a wavelength monitor (a second detector). A suitable wavelength monitor comprises an etalon, beam splitter and pair of photodiodes. The output from the processor provides a fine correction adjustment to the input current to the laser diode from the current source which reduces the wavelength error to a very low value (e.g., ~10 MHz). Prior art control methods do not achieve this precise level of wavelength control. The output of the processor is preferably the sum of a first quantity proportional to the error signal and a second quantity proportional to the integral of the input signal, the output of the processor preferably being limited to ensure that the current to the laser cannot be changed too far from the tabulated value. The wavelength monitor determines when wavelength stabilization has occurred. With our system the time required to stabilize the laser wavelength at a desired value is only a few hundred microseconds as compared to prior art designs which may require as much as 100 milliseconds. Prior art designs apparently use a fixed length cavity and set the laser temperature to an approximately correct value for the desired wavelength. The current to the laser is then modulated until the laser emits at a wavelength that fortuitously corresponds to a cavity mode. This method does not permit sufficiently precise control of the ring-down wavelength to achieve many of the more demanding and difficult analyses. In addition, the resolution capability of prior art systems is limited by the cavity free spectral range. Since the cavity length will change slightly with a change in temperature, and can randomly change up or down by one-half the free spectral range, this can adversely affect the precision of the system.

In our design, to record ring-downs, the beam path length of the cavity is continuously swept (modulated) over a range of lengths, including that at which the cavity will be in resonance with the incoming light, using, for example, a piezo-electric transducer (PZT) to translate one of the cavity mirrors as described in co-pending, commonly assigned U.S. patent application Ser. No. 10/391,928, filed Mar. 18, 2003 the disclosure of which is incorporated herein by this reference. Initially the cavity length controller is in scan mode, and the range of cavity lengths is chosen to be sufficiently large that the round trip length of the cavity changes by at least one wavelength of the optical radiation so that the comb of cavity resonance frequencies will always cover the emitted laser frequency at some point within the sweep. The sweep rate is chosen to be sufficiently slow so that the cavity fills efficiently once resonance is achieved. The cavity round trip length is changed over one wavelength in approximately 50–200 milliseconds. During the wavelength stabilization period the threshold comparator is turned off to preclude ring-down.

Once the wavelength error is sufficiently small i.e., the wavelength is sufficiently close to the desired wavelength, the cavity intensity detector signal is compared against a preset threshold to determine if there is sufficient light of the desired wavelength in the cavity to initiate a ring-down. This occurs near the time at which the cavity is resonant with the light. As soon as the threshold is reached, the first controller deactivates the optical signal and triggers the data acquisition unit to record the ring-down of the cavity intensity. Determining when the wavelength error is small can be achieved by monitoring the error signal.

After a delay period at least in excess of the ring-down time, and preferably a delay period of about five to ten ring-down times or even greater, which delay period may be either a pre-programmed, fixed time delay (which is preferred), or a delay period determined by noting when the cavity has rung-down by measuring the residual optical intensity in the cavity using the first detector, a new cycle begins by current again being sent to the laser to turn it on once again (or the laser again being caused to direct light into the cavity, as previously described).

In a typical spectroscopic measurement, several ring-downs are recorded with the laser set to the same wavelength, so that the statistical error in the ring-down time may be reduced. Instead of sweeping the cavity length over a wide range of lengths (a full scan) after the first ring-down has been detected, the range of lengths swept over is reduced so that less time is required for the resonance condition to be satisfied after the laser emission wavelength has stabilized. The means used to control the cavity length is said to be in tracking mode, and the rate of measuring ring-down times is increased preferably to several hundred sweeps per second. For small changes in the laser wavelength, the limits of the range of cavity lengths may be adjusted dynamically so that the cavity tracks the laser. When a larger change in laser wavelength occurs, it is necessary to return the cavity length controller to scan mode so that the cavity resonance may be found again.

DETAILED DESCRIPTION OF THE INVENTION

The operation of the prior art CRDS system shown in FIG. 1 has already been described.

Figure 2:
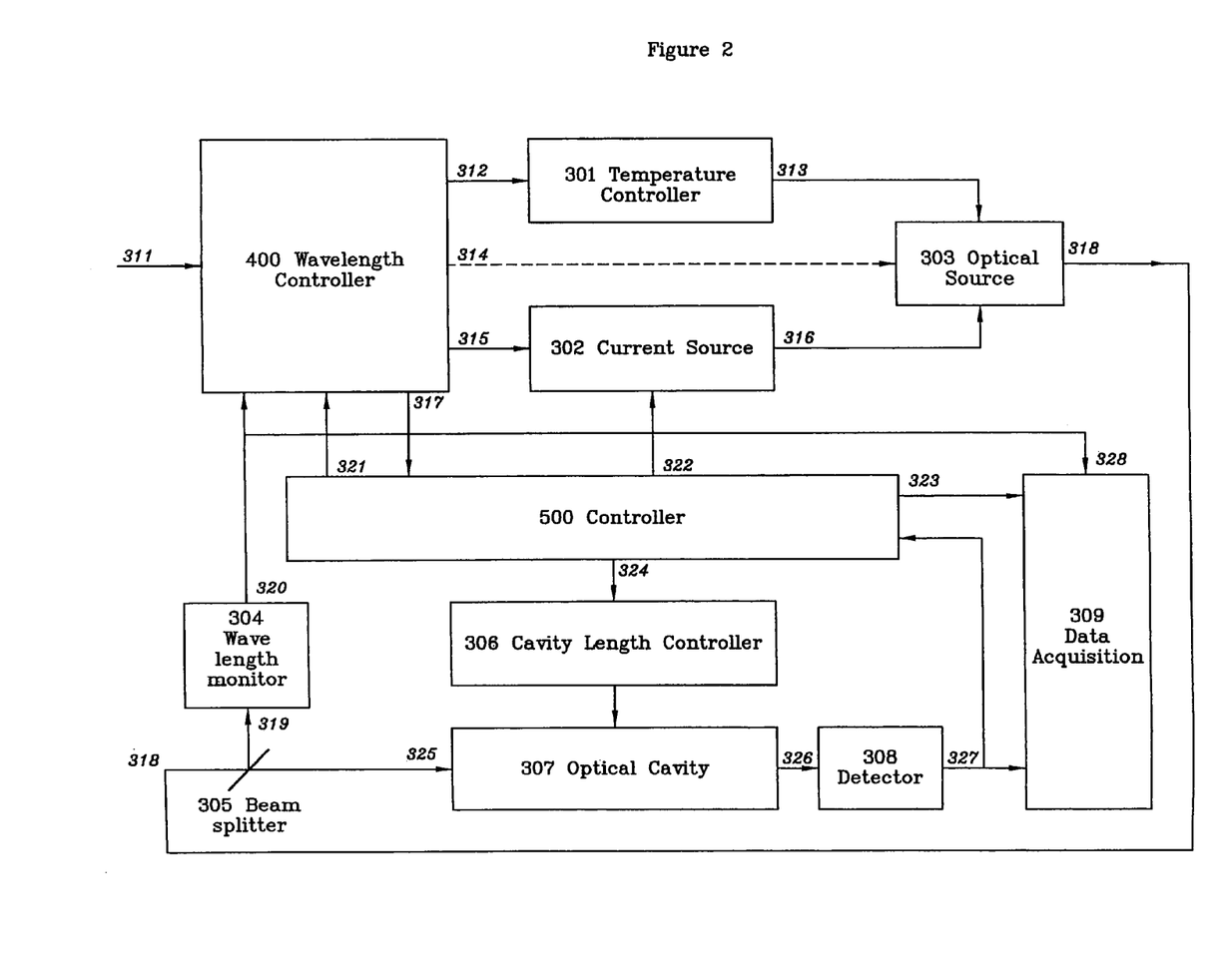
FIG. 2 is a block diagram showing the functional relationship of the main components of a CRDS system in accordance with the present invention.

FIG. 2 illustrates the major components and functioning of a CRDS system in accordance with the present invention. Starting with optical source 303, a semiconductor laser (or laser array as previously described), the laser is electrically pumped by current 316 from current source 302. Laser light 318 emitted and divided by beam splitter 305. A small portion of the light 319 is directed to wavelength monitor 304. The remaining light 325 directed into optical cavity 307. A first detector 308 monitors the level of cavity filling by measuring the amount of light 326 is passing out of one of the cavity mirrors. Detector 308 inputs the information 327 regarding the extent of cavity filling (or the ring-down signal) to a data acquisition unit 309 and a first controller 500. When detector 308 indicates that optical cavity 307 is sufficiently full, controller 500 sends signal 322 to current source 302 to deactivate optical source 303 by any of the previously indicated methods. Controller 500 substantially simultaneously instructs (signal 325) data acquisition unit 309 that a ring-down is occurring. Wavelength monitor 304 instruct (signal 328) unit 309 as to the wavelength of the light into the optical cavity at the time of the ring-down event. Additional signals to or from controller 500 are indicated by arrows 321, 317 and 324. Arrow 321 indicates to the second (wavelength) controller 400 when the current to laser 303 is turned on, so that wavelength locking may be activated.

Conversely, arrow 317 denotes a signal from controller 400 to controller 500 which ensures that a ring-down is not triggered unless the laser wavelength is at a desired value. Signal 324 from controller 500 instructs the cavity length controller 306 to sweep the cavity (by using, for example, a PZT transducer) so as to bring it into resonance with the optical source wavelength. Signal 311 indicates the desired wavelength for the ring-down, which is dependent on the nature of the target analyte. This signal is used by wavelength controller 400 to lock the optical source wavelength to the correct value.

Figure 3:
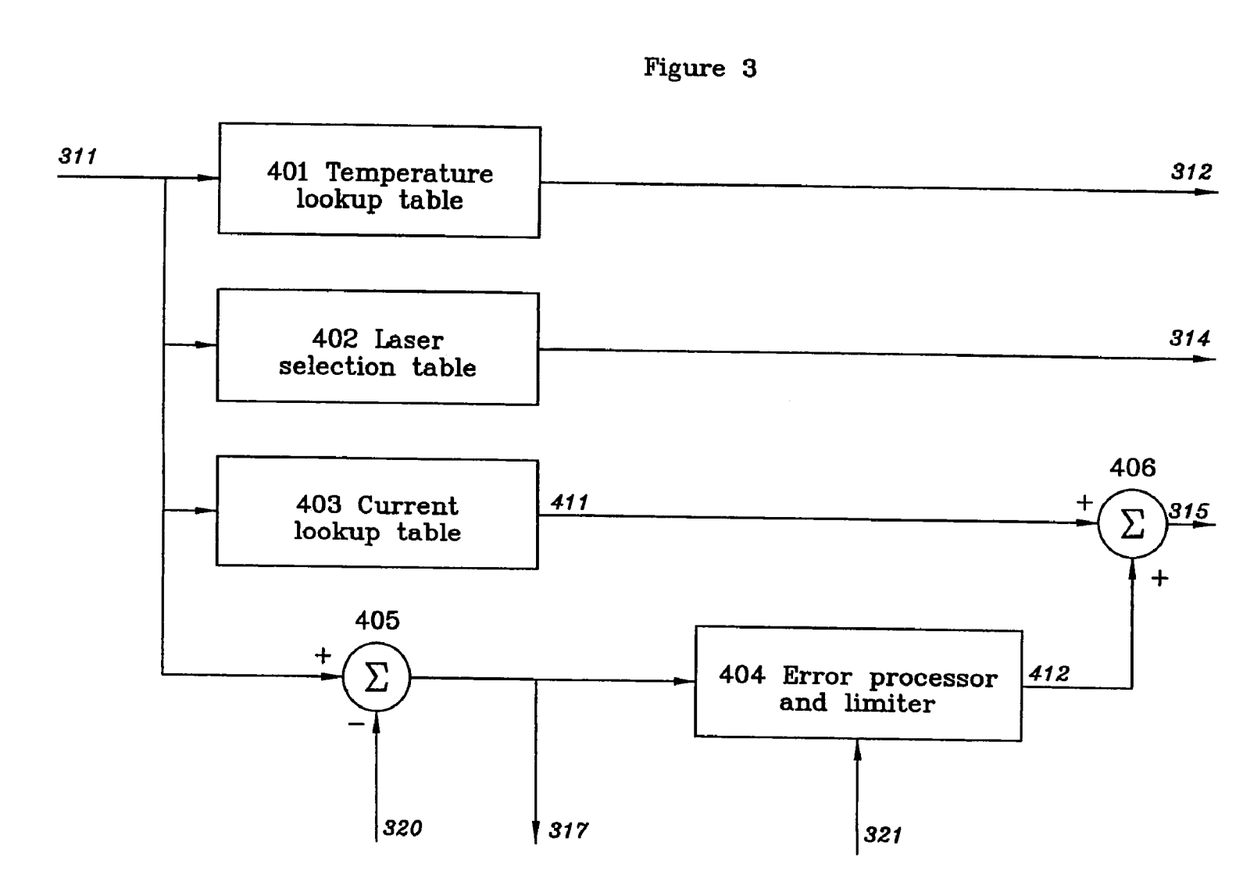
FIG. 3 is a block diagram showing details of the wavelength controller subsystem in accordance with the present invention.

FIG. 3 shows wavelength controller 400 in greater detail. As indicated, arrow 311 denotes the desired emission wavelength for the laser. Lookup table 401 indicates the temperature adjustment necessary to cause the laser to emit at approximately wavelength 311 and sends instructions 312 to temperature controller 301 which, as represented by arrow 313, adjusts the temperature of laser 303.

The present invention also contemplates a current lookup table 403 to provide the approximately correct (coarse) current value 411 for the desired emission wavelength. However, in order to obtain precise control of the wavelength, a correction of the coarse current value is derived via a comparison of the measured wavelength 320 (determined by the wavelength monitor 304) with the desired wavelength 311. Unit 405 ( a difference circuit) determines the difference between these quantities and sends the resulting error signal 317 to processor 404 and controller 500. Signal 321 from controller 500 instructs the error processor 404 to determine the fine current correction 412 which must be added to the coarse value 411 in order to produce the precise current needed to achieve the desired emission wavelength. Unit 406 (a summing circuit) carries out the required addition, and sends signal 315 to the current source 302, indicating the current which should be sent to optical source 303. Where a laser array is utilized, as represented by line 314, a multi-laser lookup table 402, is used to select the appropriate laser in the array. In this case, for each laser in the array, there is a section of temperature lookup table 401 and current lookup table 403 appropriate for the range of wavelengths covered by that particular laser.

Figure 4:
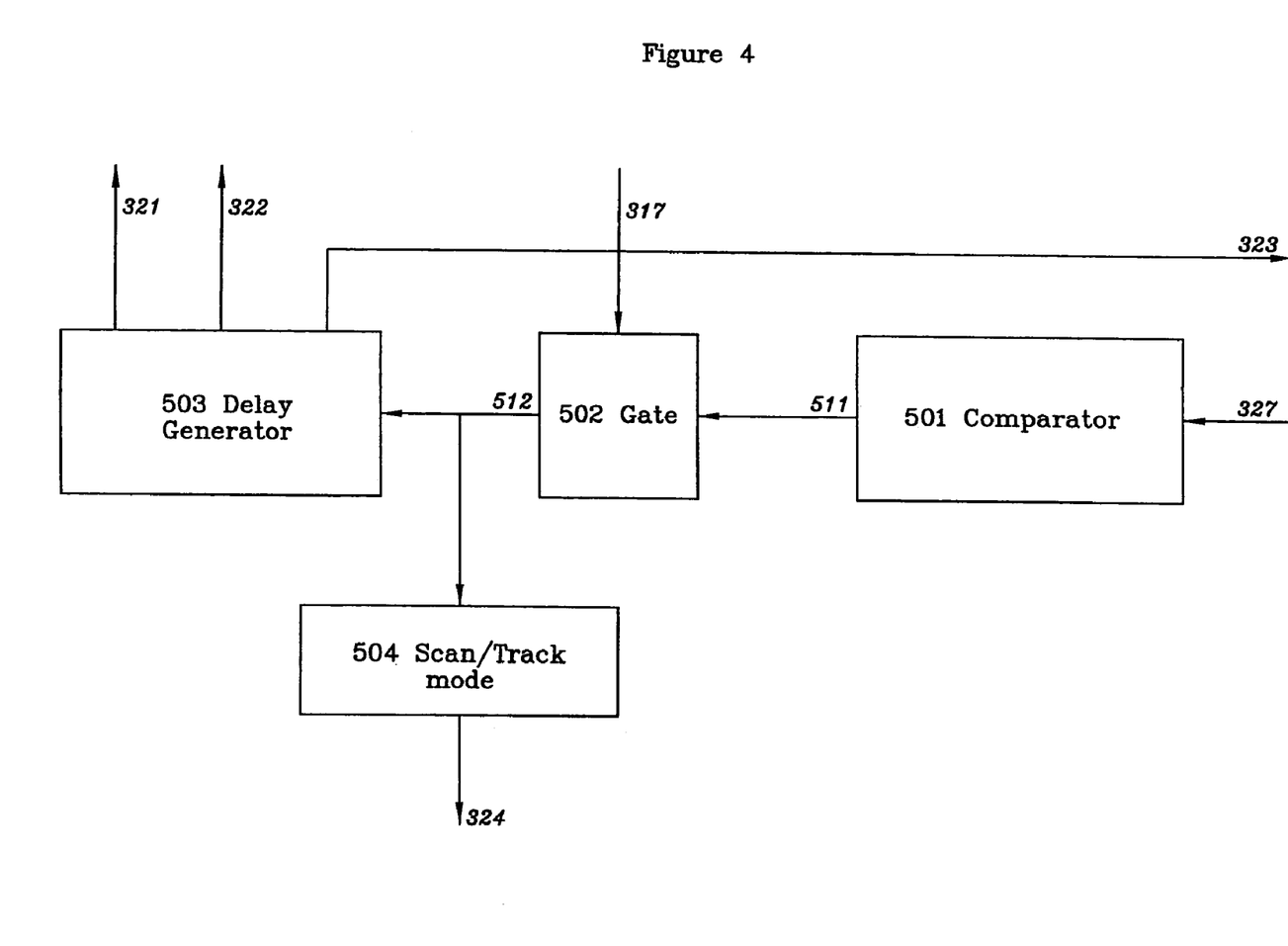
FIG. 4 is a block diagram showing details of timing and control subsystem in accordance with the present invention.

FIG. 4 provides a detailed picture of the operation of the main components of signal controller 500. Comparator 501 receives signal 327 from detector 308 and determines when the optical cavity 307 has filled above the required threshold. Logic gate 502 combines signal 511 which indicates that the threshold has been reached, with signal 317 from wavelength controller 400 which indicates that the measured wavelength 320 of the optical source is substantially equal to the desired wavelength 311. When both conditions are fulfilled, gate 502 sends signal 512 to indicate that a ring-down should be initiated by deactivating the optical source. Signal 512 instructs delay generator 503 to send signal 322 to the current source to turn off the current and also signal 321 to the wavelength controller 400 indicating that the laser is off and in both cases for what period of time. At this time delay generator 503 also sends signal 323 to data acquisition unit 309 indicating that it is now receiving valid ring-down data. Signal 512 also goes to unit 504 which, as previously described, switches from scan mode to tracking mode after the first ring-down is detected by sending signal 324 to the optical cavity length controller 306 which moves the PZT element thereby translating one of the cavity mirrors.

Figure 5:
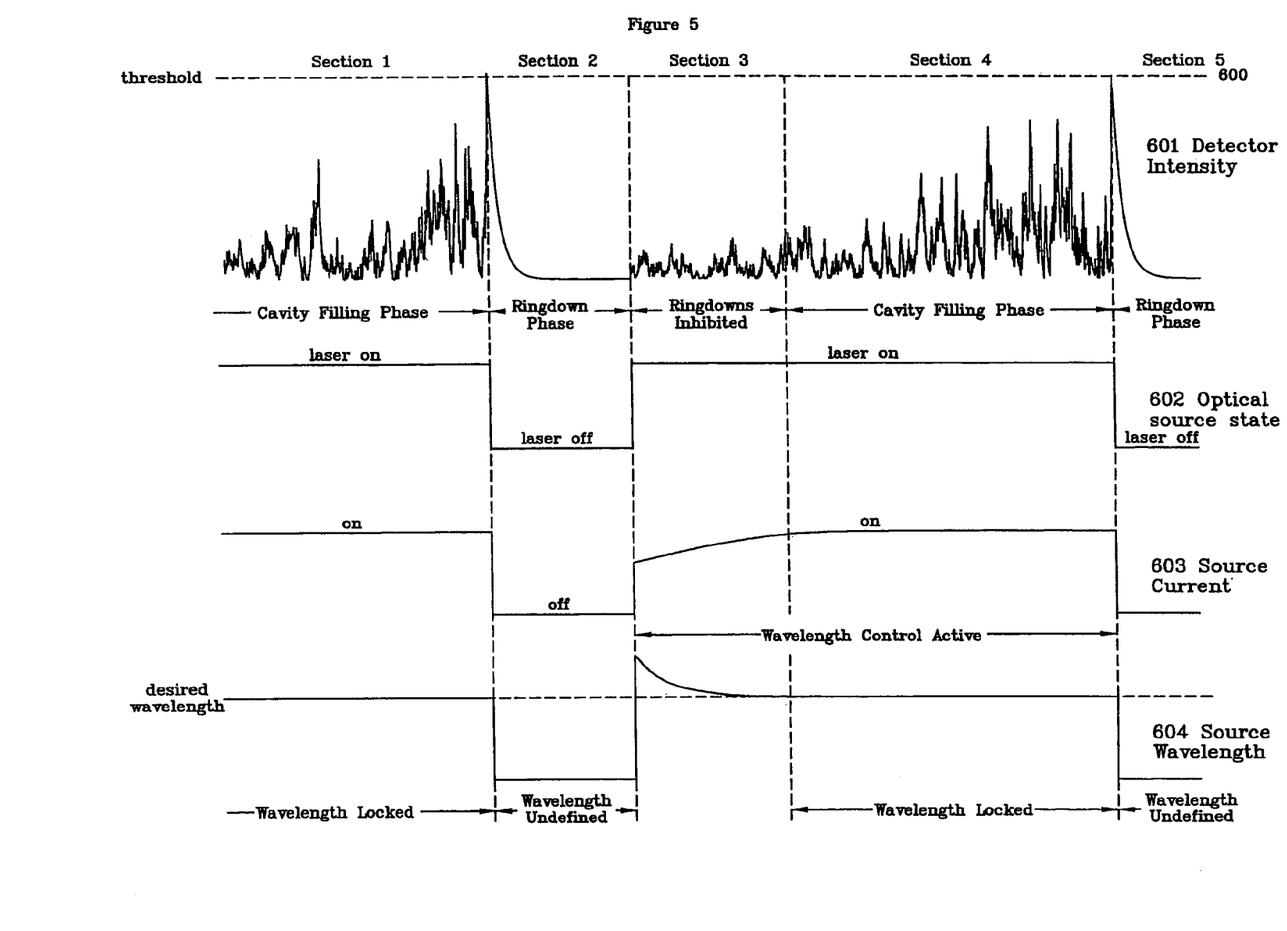
FIG. 5 is a graphical representation showing the photon content of the cavity and the laser emission wavelength at various stages of the cavity filling and ring-down process.

FIG. 5 is a time sequential diagram illustrating the operation cycle of a CRDS instrument in accordance with the present invention. The x-axis of the diagram is a time line while the y-axis indicates the status of various system components at a given portion of the cycle. Horizontal dashed line 600 indicates the light content threshold required which the cavity must reach before ring-down occurs. Starting at the left side of FIG. 5 with the segment 601 showing detector intensity, the cavity fills as shown in Section 1 and then rings-down in Section 2. In Section 3, although the optical source is providing light to the cavity, ring-down is inhibited because the wavelength is incorrect. In Section 4 the cavity fills and then rings-down again in Section 5. Correspondingly, as indicated in segment 602, the laser is on in Sections 1, 3 and 4 and off when ring-down is occurring in Sections 2 and 5. By "off" it is meant that the laser is not providing light to the resonant cavity by any of the methods prviously discussed. Segment 603 shows the status of the current to the laser, on Section 1 (the cavity filling phase) and off in Section 2 (the ring-down phase). In Section 3, the wavelength control adjusts the current to bring the emission wavelength to the precise value as indicated in Section 4. Finally Segment 604 indicates the status of the wavelength, locked during the cavity filling phase (Sections 1 and 4), no light entering the cavity during ring-down and the wavelength being brought to the desired value in Section 3.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A cavity ring-down spectrometer comprising:
   i) a resonant optical cavity comprising at least two high reflectivity mirrors;
   ii) a source for providing a continuous wave optical signal into said optical cavity, said source comprising an electrically pumped semiconductor gain medium;
   iii) a first detector for monitoring the intensity of radiation emitted from said cavity and generating a first detection signal based thereon;
   iv) a first controller for deactivating said optical signal based on a comparison of said first detection signal and a predetermined threshold and for thereafter reactivating said optical signal after a delay period in excess of the ring-down time for said optical cavity;
   v) a second detector for monitoring the wavelength of the reactivated optical signal and generating a second detection signal based thereon;
   vi) a second controller coupled to said second detector which second controller adjusts both the temperature of, and the current to, said gain medium to thereby achieve a desired emission wavelength;
   vii) means for adjusting the beam path length of the optical cavity to be in resonance with said desired emission wavelength.

2. A cavity ring-down spectrometer in accordance with claim 1 wherein said optical signal source comprises at least one distributed feedback diode laser.

3. A cavity ring-down spectrometer in accordance with claim 1 wherein said optical signal source comprises an array of lasers.

4. A cavity ring-down spectrometer in accordance with claim 1 wherein said first detector comprises a photodiode or avalanche photodiode.

5. A cavity ring-down spectrometer in accordance with claim 1 wherein said first controller includes means for deactivating said optical signal by terminating the current flow to said semiconductor gain medium.

6. A cavity ring-down spectrometer in accordance with claim 5 wherein said current flow is terminated by shunting the current to an alternative medium.

7. A cavity ring-down spectrometer in accordance with claim 1 wherein said first controller includes means for shifting the frequency of said optical signal to a value out of the resonance range of the optical cavity.

8. A cavity ring-down spectrometer in accordance with claim 1 wherein said second detector comprises an etalon, a beam splitter and a pair of photodiodes.

9. A cavity ring-down spectrometer in accordance with claim 6 wherein said resonant optical cavity comprises three or four mirrors.

10. A cavity ring-down spectrometer in accordance with claim 1 wherein said second controller includes means for substantially continuously monitoring the temperature of the gain medium, and look-up tables indicating the temperature and current required to cause a desired laser emission wavelength.

11. A cavity ring-down spectrometer in accordance with claim 1 wherein said means for adjusting the beam path length of the optical cavity comprises a piezo-electric transducer capable of translating one of the cavity mirrors.

12. A method for detecting the presence of an analyte in a resonant optical cavity comprising at least two high reflectivity mirrors, said method comprising the steps of:
  i) directing a continuous wave optical signal from an electrically pumped semiconductor gain medium into said optical cavity;
  ii) detecting radiation emitted from said optical cavity through one of said mirrors and comparing the intensity of said emitted radiation with a predetermined threshold value;
  iii) based on said comparison, generating a control signal which deactivates said optical signal for a period which is at least in excess of the ring-down time for said optical cavity;
  iv) reactivating said optical signal and again directing said signal into said optical cavity
  v) monitoring the wavelength of said signal;
  vi) adjusting the temperature of, and current to, the source of said optical signal to thereby cause it to emit a signal having a desired wavelength;
  vii) adjusting the beam path length of said optical cavity by translating at least one of said mirrors to thereby bring said cavity into resonance with said desired wavelength optical signal.

13. A method in accordance with claim 12 wherein said optical signal is deactivated for a period of at least about five ring-down times.

14. A method in accordance with claim 12 wherein said optical signal is deactivated by interrupting the current flow to said gain medium.

* * * * *